(12) United States Patent
Mie et al.

(10) Patent No.: US 8,563,322 B2
(45) Date of Patent: Oct. 22, 2013

(54) METHOD FOR SEPARATION OF MOLECULES

(76) Inventors: Axel Mie, Aelvsjoe (SE); Curt Reimann, Lund (SE); Magnus Jornten-Karlsson, Lund (SE); Bengt-Olof Axelsson, Lund (SE)

(*) Notice: Subject to any disclaimer, the term of this patent is extended or adjusted under 35 U.S.C. 154(b) by 695 days.

(21) Appl. No.: 12/297,742

(22) PCT Filed: Apr. 20, 2007

(86) PCT No.: PCT/SE2007/000382
§ 371 (c)(1),
(2), (4) Date: Mar. 26, 2009

(87) PCT Pub. No.: WO2007/123464
PCT Pub. Date: Nov. 1, 2007

(65) Prior Publication Data
US 2009/0224147 A1    Sep. 10, 2009

Related U.S. Application Data

(60) Provisional application No. 60/795,469, filed on Apr. 28, 2006.

(30) Foreign Application Priority Data

Apr. 20, 2006   (SE) .................................... 0600862

(51) Int. Cl.
*G01N 24/00* (2006.01)
(52) U.S. Cl.
USPC ........... 436/173; 250/281; 250/282; 250/283; 250/284; 250/285; 250/286; 250/287; 250/288

(58) Field of Classification Search
None
See application file for complete search history.

(56) References Cited

U.S. PATENT DOCUMENTS

| | | | | |
|---|---|---|---|---|
| 5,254,258 | A * | 10/1993 | Pirkle et al. | 210/643 |
| 7,015,462 | B2 * | 3/2006 | Karas | 250/287 |
| 2003/0057369 | A1 | 3/2003 | Guevremont | |
| 2005/0109930 | A1 * | 5/2005 | Hill et al. | 250/286 |
| 2008/0173809 | A1 * | 7/2008 | Wu | 250/283 |

FOREIGN PATENT DOCUMENTS

| | | |
|---|---|---|
| CA | 2273322 A1 | 2/2000 |
| WO | 00/08454 A1 | 2/2000 |
| WO | 02/096805 A2 | 12/2002 |

OTHER PUBLICATIONS

Clowers, B.H., et al. Influence of cation adduction on the separation characteristics of flavonod diglycoside isomers using dual gate-ion mobility-quadrupole ion trap mass spectrometry, 2006, Journal of Mass Spectrometry, vol. 41, pp. 339-351.*

(Continued)

*Primary Examiner* — Robert Xu
(74) *Attorney, Agent, or Firm* — Nields, Lemack & Frame, LLC

(57) ABSTRACT

A method for separating molecules, such as enantiomers, other stereoisomers and constitutional isomers by ion mobility spectrometry (IMS). Molecules of interest are ionised after addition of a suitable chiral reference compound, resulting in the formation of cluster ions that can be separated by IMS techniques such as ion drift mobility (IDM) spectrometry or FAIMS. This method allows, for example, for fast and sensitive quantification of one enantiomer in presence of an excess of the other enantiomer.

15 Claims, 6 Drawing Sheets

(56) References Cited

OTHER PUBLICATIONS

Leavell, Conformational Studies of Zn-Ligand-Hexose Diastereomers Using Ion Mobility Measurements and Density Functional Theory Calculations, 2002, 13, 284-293, J Am Soc Mass Spectrom.

Shizuma, Facile ee-determination from a single measurement by fast atom bombardment mass spectrometry: a double labeling method, 2001, 210/211, 585-590, International Journal of Mass Spectrometry.

Grigorean, A Mass Spectrometry Method for the Determination of Enantiomeric Excess in Mixtures of d,l-Amino Acids, 2000, 72 (18), 4275-4281, Analytical Chemistry.

Tao, Kinetic Resolution of D,L-Amino Acids Based on Gas-Phase Dissociation of Copper (II) Complexes, 1999, 71 (19), 4427-4429, Analytical Chemistry.

Sultan, Structural Identification of Highly Polar Nontarget Contaminants in Drinking Water by ESI-FAIMS-Q-TOF-MS, 2006, 78, 2905-2917.

* cited by examiner

| Analyte enantiomers | Successful combinations of metal and reference compounds |
|---|---|
| D/L-Trp | $Zn^{2+}$/L-Gln, $Zn^{2+}$/L-Pro, $Mg^{2+}$/L-Arg, $Ni^{2+}$/L-Asn, $Cu^{2+}$/L-Gln, $Cu^{2+}$/L-Lys |
| D/L-Pro | $Zn^{2+}$/L-Asn, $Ni^{2+}$/L-Gln |
| D/L-Phe | $Mg^{2+}$/L-Val, $Mg^{2+}$/L-Pro, $Ni^{2+}$/L-Pro, $Ni^{2+}$/L-Lys, $Cu^{2+}$/L-Pro, $Cu^{2+}$/L-Gln |
| D/L-Val | $Mg^{2+}$/L-Ile, $Cu^{2+}$/L-Trp |
| D/L-Met | $Cu^{2+}$/L-Phe, $Ni^{2+}$/L-Asn |
| D/L-Arg | $Ni^{2+}$/L-Met, $Ni^{2+}$/L-Val, $Cu^{2+}$/L-Gln, $Cu^{2+}$/L-Lys, $Mg^{2+}$/L-Trp |
| D/L-Lys | $Cu^{2+}$/L-Ile, $Cu^{2+}$/L-Val |

Figure 6

METHOD FOR SEPARATION OF MOLECULES

This application is a 371 of PCT/SE2007/000382 filed Apr. 20, 2007, which claims priority of U.S. Provisional Application Ser. No. 60/795,469 filed Apr. 28, 2006 and claims priority of Swedish Application No. 0600862.7 filed Apr. 20, 2006, the disclosures of which are hereby incorporated by reference.

AREA OF INVENTION

The instant invention relates to a method for separating molecules, such as enantiomers as well as other isomers in the gas phase, based on ion mobility spectrometric (IMS) techniques such as high-field asymmetric waveform ion mobility spectrometry (FAIMS) or ion drift mobility (IDM) spectrometry.

BACKGROUND OF INVENTION

Ion mobility spectrometry (IMS) comprises a family of techniques for separating ions on the basis of their mobility in the gas phase. Ion drift mobility (IDM) spectrometry was introduced as an analytical technique in the beginning of the 1970's, although ion mobility research had been carried out for several decades previously, mostly for ion characterisation. In the 1980's, the first analytical instrument based on field-asymmetric ion mobility spectrometry (FAIMS) principles was described.

Throughout this document, IMS will refer to all techniques that have the capability of separating ions in the gas phase on the basis of their ion mobility characteristics. One such technique is "classical" ion drift mobility (IDM) spectrometry in which ion separation occurs in a static, homogeneous axial electric field. By contrast, another such technique, FAIMS, is based on an asymmetrical time-alternating electric field, which is transverse to the net direction of ion motion in a flowing bath gas. These features will be clarified before presenting the scope of the instant invention.

In ion drift mobility spectrometry, pulses of ions (ion "packets") are typically introduced into a gas-containing tube with a static, axial, and ideally constant electric field E that drags the ions through the bath gas. An ion packet composed of ions characterized by mobility K will "drift" with constant speed $v=K\cdot E$ (with a small correction for diffusion). If the ion packet contains components characterized by differing ion mobility values K, these components acquire different speeds. Consequently, the ions are separated according to their ion mobility values. When recording the time profile of the intensity of ions arriving at a detector after introducing an ion packet into the drift tube at a well-defined time, an ion mobility spectrum is obtained. This ion mobility spectrum reflects the range of mobility values possessed by the ions comprising the ion packet. Mobility also depends on an ion's charge state. Of greater significance and utility, mobility depends on the detailed interactions between analyte ion and bath gas, as reflected by the orientationally-averaged collision cross section. Thus, the range of mobility values observed in an IDM experiment can reflect different conformations of the same ion (e.g. same chemical formula and covalent connectivity, as in proteins of different conformation); different structures of constitutional isomers (e.g. same chemical formula but different covalent connectivity as in carbon clusters); or different arrangement in space of the atoms of diastereomers; or it can reflect the presence of a number of completely different ions (e.g. ions of different structures and compositions). Normally, but not necessarily, electric fields in IDM are relatively weak, so that ions have an ion mobility $K=K_o$ that is independent of the electric field strength E.

In its most widespread design, an IDM instrument features a drift tube with evenly-spaced concentric drift rings carrying different voltages along the interior of the drift tube, ensuring the presence of a constant axial electric field of negligible inhomogeneity along and near the central axis.

FAIMS exploits the fact that, at sufficiently high electric fields, most ion species display a dependence of their ion mobility on the electric field strength—the mobility is no longer electric-field-independent, $K=K(E)$. If we express $K(E)$ as $K_0\cdot(1+h[E])$, the function $h(E)$ will vary depending on the structure and identity of the ion. FAIMS separates ions characterized by differing ratio of high-field mobility to low-field mobility—i.e. ions are separated according to the quantity $1+h(E)$. This is done by alternating a high electric field of one polarity during a short time, with a low electric field of the opposite polarity during a longer time. In such a scheme, ions would oscillate and return to their starting positions after each cycle, if it were not for the dependence of the ion mobility on the electric field strength. This dependence gives each ion a net non-zero displacement during each cycle. Typically, FAIMS separation takes place between two parallel plates or between two concentric cylinders with a spacing of a few millimeters. An axial (or longitudinal) gas flow sweeps the ions along a path roughly parallel to the axial direction, while the applied electric field causes transverse ion motion roughly perpendicular to the gas flow. When cylindrical electrodes are employed, FAIMS features an additional ion focusing effect because the electric field between the cylinders possesses a gradient.

FAIMS separation is driven by the dispersion voltage (DV), a high-voltage asymmetric waveform that is applied between the two electrodes. By applying an additional constant but adjustable compensation voltage (CV), the net displacement of a certain ion species during each DV waveform cycle can be compensated, resulting in those ions being transmitted through the FAIMS while non-compensated ions are lost in collisions with the electrode surfaces. By scanning CV and measuring the transmitted ions at the ion outlet, data can be obtained in the form of a "CV spectrum". Alternatively, the CV can be kept constant or can be cycled over a few predetermined values, so as to only transmit ions of interest.

Both IDM spectrometry and FAIMS can be operated at different gas pressures, gas temperatures and gas compositions. Both IDM spectrometry and FAIMS have been proposed and/or shown to work with different ion sources, including electrospray ionisation (ESI), nanospray ionisation (nESI), ionspray, atmospheric pressure chemical ionisation (APCI), matrix-assisted laser desorption-ionisation (MALDI), and beta emitter ionisation. Other ionisation techniques could be used as well. Both IDM spectrometry and FAIMS have been coupled to different detectors, such as mass spectrometers (MS), and charge-measuring devices like a Faraday plate coupled to an electrometer. One big difference between IDM spectrometry and FAIMS is that IDM spectrometry typically is a pulsed technique, relying on an ion flight time to link a mobility value with a particular sub-population of ions, while FAIMS is a continuous-flow technique that can be set to allow continuous passing of a distinct population of ions characterized by a certain relation between high-field and low-field mobility. Ion drift mobility spectrometry and FAIMS principles and applications are described in exhaustive detail by Eiceman and Karpas in their book "Ion Mobility Spectrometry", $2^{nd}$ Edition (2005), CRC Press, Boca Raton, Fla.

Different structural isomers and stereoisomers of molecules often feature different physical, chemical and biological properties. It is therefore of importance that analytical chemistry promote the development of tools to distinguish between different isomers. One group of stereoisomers, the enantiomers, is of specific interest because two enantiomers have different chemical properties only in asymmetric environments. Life itself offers one of the key examples of asymmetric environments—and many cases are known for which two enantiomers have very different effects on biological systems. One example is drug substances where one enantiomer has a therapeutic effect while the other enantiomer has an adverse effect. It is a challenge for analytical chemists to be able to develop techniques that can either separate enantiomers or else reliably detect one such enantiomer in the presence of another—even in cases where there is a large concentration difference.

Another area in which isomers are of key importance is carbohydrate chemistry. Carbohydrate monomers exist as a large variety of structural isomers and stereoisomers, and carbohydrate oligomers and polymers display an even greater variety. To understand the relationship between structure and property of carbohydrates, and to be able to develop and manufacture new products from carbohydrates like starch and cellulose, new analytical techniques are needed that can distinguish between different isomers. For example, the separation and analysis of sugar dimers of the same mass, but of different stereochemistry, poses a great challenge when employing existing techniques.

The most widely employed approach for separation of enantiomers is liquid chromatography (LC) with chiral stationary phases. Capillary electrophoresis, capillary electrochromatography and gas chromatography are also employed in chiral separations. While useful in many cases, chromatography is often time-consuming. The chiral phases employed are also said to be "less rugged". Another approach for determining enantiomeric excess in samples is NMR. Some kind of chiral shift reagent is required, along with fairly copious amounts of sample. Although useful for some problems, none of these techniques comprises a general solution for the analysis of enantiomers.

Guevremont et al. (WO 00/08454) ("Guevremont") propose a "method for separation of isomers and different conformations of ions in gaseous phase" using FAIMS. Analytes are ionised and subjected to FAIMS separation. Guevremont includes enantiomers in their list of analytes that can be separated with the aid of FAIMS; however, they do not give any examples for separated enantiomers. It seems doubtful that their method alone can separate enantiomers, as enantiomers can only be separated in an asymmetric chemical environment, and their method lacks such asymmetric elements.

Tao et al. (Analytical Chemistry, Vol. 71, No. 19, 1999) ("Tao"), and others, have proposed a mass spectrometric method that leads to the quantification of enantiomers by providing just such an asymmetric environment. In this method, trimeric cluster ions containing one metal ion, two molecules of an enantiopure reference compound, and one molecule of a chiral analyte compound are formed by association in solution phase. Cluster ions containing one enantiomer of the analyte versus the other enantiomer of the analyte are considered to be diastereomeric. These cluster ions are electrosprayed and subjected to tandem (fragmentation) mass spectrometry. From the relative intensities of certain of the formed fragment ions, conclusions can be drawn about the enantiomeric excess of one enantiomer analyte over the other, when the reference compound and metal ion have been suitably selected. Often a notable chiral sensitivity can be achieved. This method does not lead to a physical separation of diastereomeric cluster ions prior to mass analysis, since both diastereomeric cluster ions are detected at the same time and mass-to-charge ratio. Rather, the relative amount of the enantiomer analytes is reflected indirectly in the fragmentation pattern through the energetics of fragmentation of the diastereomers. Advantages of the technique include its simplicity, the need for only small amounts of material, and the tolerance of the method to the presence of background impurities. One drawback is the relatively high uncertainty of the measurement, typically at one or a few percent of enantiomeric excess, limiting the usefulness of the method in case very small amounts of one enantiomer are present in a large excess of the other enantiomer.

Different approaches combining host-guest systems with mass spectrometric measurements in order to analyse enantiomers have been described as well. Generally, in this method, a large chiral molecule (host) interacts non-covalently with a small chiral analyte (guest) in a stereoselective way. Mass spectrometric determination of the enantiomeric excess is then performed e.g. with the help of isotope labelled/unlabelled chiral host pairs and isotope labelled internal standards (e.g. Shizuma et al., Int. J. Mass Spectrom. 2001, 210/211, 585-590), or by stereoselective gas-phase exchange reactions (e.g. Grigorean et al., Anal. Chem. 2000, 72, 4275-4281).

Karas (WO 02096805) ("Karas") proposes an ion drift mobility spectrometric method for separating enantiomers and other isomers and compounds, "using a supply of selectively interactive gaseous particles" as "separating substance". For the case of enantiomer separation, in the first preferred embodiment of the patented idea, chiral gaseous molecules are added to the bath/drift gas for collisions, which undergo clustering/declustering interactions with the chiral analyte ions. In case one enantiomer has a stronger interaction with the neutral chiral collision molecules (i.e. separation particles) than the other enantiomer, the retention time of the first enantiomer in an IDM experiment would be prolonged, because said first enantiomer would presumably display a higher time-averaged collision cross section due to clustering with the chiral gas molecule. In the second preferred embodiment of the patented idea, the gaseous particles used for selective interactions with the enantiomers (or other compounds) are macroscopic particles such as macromolecules or nanoparticles, possibly ones with smaller chiral molecules bound to said particles surfaces, intended to provide a local chiral environment to which enantiomers may be bound in interaction processes for different periods of time depending on their chirality. These particles are added into the bath/drift gas as described just above. Again, the separation according to this invention relies on differences of the affinity or timescale of interaction between the two enantiomers and the separating particles as sampled via collisional interactions, driving a difference in drift time that separates the chiral enantiomers. It is a characteristic of the patented idea that such "separating substances", "which comprises gaseous particles which selectively interact with the molecules of the components to be separated", are in fact not present in the sample, but are supplied separately to the bath gas, in order to selectively interact in collisions with the analytes of interest. It is characteristic for Karas' invention that the reference substance is provided to the IDM apparatus continuously, as long as analytes are present in the apparatus. In Karas' invention, all interactions between analytes of interest and the separating substance have the nature of collisions or temporary short-lived associations. Unfortunately, it is not obvious that a useful degree of separation has taken place in the example presented in Karas' patent.

Leavell et al. (J Am Soc Mass Spectrom 2002, 13, 284-293), and others, show the separation of diastereomers by IDM, without the addition of chiral reference compounds.

A number of techniques are used in order to separate or analyse constitutional isomers and different forms of stereoisomers, e.g. liquid chromatography and NMR. However, new approaches capable of distinguishing between isomers are still of importance.

It is a limitation of the prior art that small amounts of one enantiomer in presence of a large excess of the other enantiomer cannot be rapidly determined using a small amount of sample.

It is a limitation of the prior art that constitutional isomers and stereoisomers often are not readily separable with existing techniques.

DISCLOSURE OF THE INVENTION

Accordingly, an object of the present invention is to mitigate, alleviate or eliminate one or more of the above-identified deficiencies and disadvantages singly or in any combination.

According to an aspect of the invention, there is provided a method for separating molecules, comprising the steps of:

a) providing a sample comprising at least one first molecular species, and providing at least one chiral molecular species, b) adding said at least one chiral molecular species to said sample before ionisation, c) providing at least one ionisation source for generating ions from said sample, d) separating said generated ions on the basis of their molecular characteristics.

The first molecular species may be an isomeric molecular species.

A significant fraction of said generated ions may be cluster ions. The cluster ions may be composed of at least one isomeric molecule and at least one chiral molecule. The ions may be present in the gas phase.

In an embodiment, the separation may be provided by an ion mobility spectrometry apparatus.

The method may be used with solid or liquid samples.

The at least one first molecular species may be at least one of the groups of constitutional isomers, enantiomers, and diastereomers. The at least one isomeric species may be at least one of a pair of enantiomers. A FAIMS apparatus may be used as IMS apparatus.

In another embodiment, the method may further comprise the addition of at least one non-chiral compound, such as metal ions in solution, to said sample.

In a further embodiment, the method may further include providing an analytical instrument, such as a mass spectrometer or an electrometer, for identifying or quantifying ions, or providing a means for collecting ions, said analytical instrument or means for collecting ions being in communication with at least one ion outlet of said ion mobility spectrometer, in order to allow for analysis or recovery of ions transmitted by said ion mobility spectrometry apparatus.

The method can be used for quantifying the enantiomeric excess of a compound in a sample of interest.

The ionisation source can be chosen from the group of electrospray ioniser, atmospheric pressure chemical ioniser, beta-emitter, or MALDI.

BRIEF DESCRIPTION OF DRAWINGS

Further objects, features and advantages of the invention will become apparent from the following detailed description of embodiments of the invention with reference to the drawings, in which:

FIG. 6 shows a summary of successful enantiomer separations of 7 pairs of enantiomers, using the method disclosed herein.

DETAILED DESCRIPTION OF EMBODIMENTS

Figure 1:
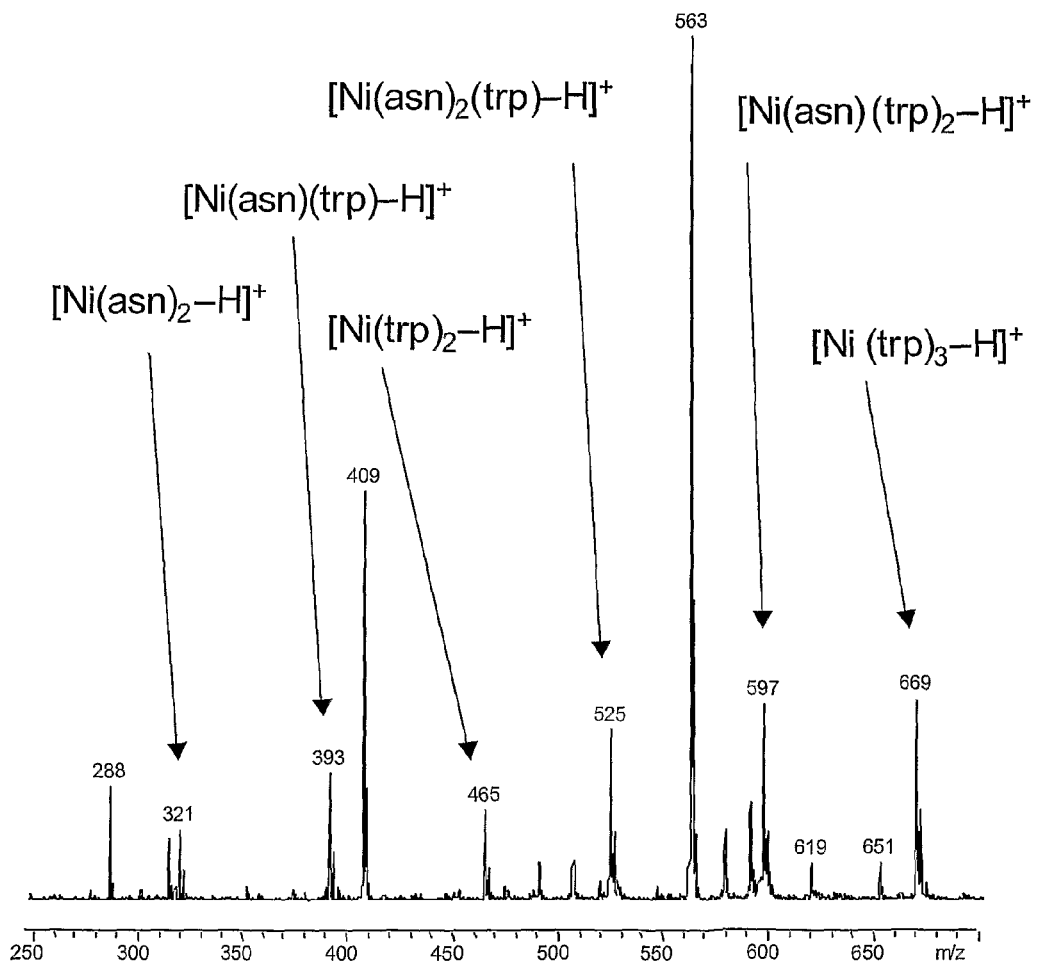
FIG. 1 is a mass spectrum diagram obtained from a mixture of L-tryptophan, D-tryptophan, L-asparagine, and nickel.

Below, several embodiments of the invention will be described with references to the drawings. These embodiments are described in illustrating purpose in order to enable a skilled person to carry out the invention and to disclose the best mode. However, such embodiments do not limit the invention. Moreover, other combinations of the different features are possible within the scope of the invention.

Generally, all terms used in the description and claims are to be interpreted according to their ordinary meaning in the technical field, unless explicitly defined otherwise herein. All references to "a/an/the [element, device, component, means, step, reference compound, ion etc.]" are to be interpreted openly as referring to at least one instance of said element, device, component, means, step, reference compound, ion etc., unless explicitly stated otherwise.

Throughout this document, a molecule is called "chiral" if it is not superimposable to its mirror image. The term "isomers" refers to compounds with the same molecular formulae, but with the atoms being arranged in different ways. Isomers fall into two main groups, constitutional isomers and stereoisomers. Constitutional isomers differ in the connectivity between atoms. Stereoisomers have the same connectivity between atoms but their arrangement in space is different; all chiral compounds thus have stereoisomers. Two stereoisomers are called enantiomers, if they are mirror images of each other, and diastereomers, if they are not mirror images of each other. Enantiopure substances contain only one of a pair of enantiomers. "Isomeric" compounds are accordingly compounds that occur as different constitutional isomers and/or stereoisomers.

The term "ion" refers to atoms, molecules or particles carrying electrical charge of positive or negative polarity. The term "cluster" refers to associated atoms, molecules and ions, bound by non-covalent or weak covalent interactions. Specifically, the term "cluster" comprises chemical complexes. The term "reference compound" refers to a chiral compound, generally enantiopure, that is used for the formation of diastereomeric clusters. Consequently, a "reference molecule" refers to one molecule of a certain reference compound. Whenever the addition, presence, etc. of a "reference compound" is mentioned in this document, it refers to the addition, presence, etc. of at least one chiral compound. Both addition of other non-chiral compounds that aid in the formation of clusters or in the ionisation process, as well as loss of small fragments such as e.g. water or protons during cluster formation or ionisation, are regarded to be normal events and are thus not generally mentioned explicitly. It should be noted, though, that in many cases the addition of other non-chiral compounds is of crucial importance for the formation of clusters. For example, metal ions and non-chiral chelating agents are useful compounds for the formation of clusters that can be separated according to the method described herein; however, the addition of non-chiral compounds alone to a mixture of two enantiomers cannot lead to separation according to the method described herein. Thus, whenever the addition, presence etc. of a reference compound is mentioned, this potentially includes the addition, presence etc of one or more non-chiral compounds along with one or more chiral reference compounds.

Throughout this document, the term "ion mobility" refers to the mobility coefficient K for ions in the gas phase in an electric field E, according to v=K·E, v representing an ion's speed. This implies that in a given system, the gas is dense enough that the ions rapidly reach a terminal speed; ion acceleration by the electric field and energy loss during ion collisions with gas molecules balance each other out over time. The term "ion mobility spectrometry" (IMS) refers to all techniques that have the capability of separating ions in the gas phase on the basis of their ion mobility characteristics. "Ion drift mobility (IDM) spectrometry" refers to techniques that separate ions on the basis of differences of their actual ion mobility, preferentially at low enough fields for which K is field-independent, $K=K_0$. By contrast, "field-asymmetric waveform ion mobility spectrometry (FAIMS)" refers to techniques that separate ions on the basis of differences in the ratio of their high field ion mobility relative to low field ion mobility. Accordingly, IDM spectrometry and FAIMS both are ion mobility spectrometric techniques, but they probe and are sensitive to different aspects of ion mobility.

Throughout this document, the term "analyte" refers to a compound of interest, in any context, not restricted to chemical analysis. The term "analyte" is primarily used because the experiments described herein are of analytical-chemical nature. However, whenever the term "analyte" is mentioned, it could refer to compounds of interest in other situations than analytical-chemical as well. For example, it could refer to compounds which would be of interest to characterize from a physico-chemical perspective, or which are of interest for recovery as pure substances. The term "clusters of interest" refers to clusters that contain at least one analyte molecule and at least one reference molecule. Not all clusters of interest lead necessarily to separation according to the method described herein. In order to lead to a successful separation, clusters of interest containing different isomers of the analyte should be separable by IMS according to the method described herein.

The core of the current invention is that enantiomers participate in the formation of diastereomeric cluster ions that can be separated by ion mobility spectrometry. Considering a pair of enantiomers not forming diastereomeric cluster ions: such a pair of enantiomeric ions are not separable directly by ion mobility spectrometry. This is because enantiomers are only separable in an asymmetric chemical environment, the asymmetry here referring to asymmetric interactions with other molecules. Put in other words, to be separable, the two enantiomers have to interact with a chiral environment in a way that is different for each of the two enantiomers. In ion mobility spectrometry enantiomeric ions have identical ion mobility characteristics when using non-chiral bath gases like helium, nitrogen, and others, because of a lack of such an asymmetric chemical environment. The approach described in this document bypasses the fundamental inseparability of enantiomers by exploiting formation of diastereomeric cluster ions from enantiomers with the help of chiral reference compounds. Diastereomeric ions do not generally have identical ion mobility characteristics presumably because of structural differences, and are thus potentially separable by ion mobility spectrometry.

According to the method disclosed herein, a sample is provided containing at least one chiral analyte of interest, and at least one chiral reference substance is added to said sample. Clusters may form in the sample, or during ionisation, which the sample is subjected to after the addition of the reference substance. Formed ions are subjected to ion mobility spectrometry. Among the formed ions there may be cluster ions that have different ion mobility characteristics depending on which chiral analyte is present in the cluster, and by exploiting this fact with IMS and separating said cluster ions, effectively chiral analytes are physically separated.

As an example, said cluster ion could be composed of one metal ion, one molecule of one of a pair of enantiomers, and two molecules of a chiral reference compound.

For example, a chiral reference compound and a compound containing metal ions, such as a salt solution, can be added to a sample containing a pair of amino acid enantiomers. As a result, different clusters form in the sample, among them two types of diastereomeric clusters consisting of one metal ion, two chiral reference molecules, and one molecule of one of said pair of amino acid enantiomers. The sample is then ionised by electrospray, forming, among other ions, a pair of diastereomeric cluster ions. These clusters have potentially different ion mobility characteristics and thus potentially can be separated in IDM or FAIMS.

Generally, it is not the separation itself that is of interest, but rather, the fact that the separation opens new possibilities for example for sensitive qualitative and quantitative analyses, and for the collection and recovery of enantiopure compounds.

It should be noted that the method disclosed in this document is based on the formation of clusters that have a substantial stability in the gas phase. If at all occurring, declustering, here referring to the loss of at least one reference molecule or the analyte molecule from the cluster, should be rare. A significant fraction of the initially formed clusters of interest should survive the IMS separation; "significant fraction" meaning enough clusters to allow for meaningful analysis, recovery or other experiment, as specified or required in a given experimental context. Clusters that disintegrate while passing the IMS apparatus are very unlikely to reconstitute, as no high concentration of either analytes or reference compounds are present in the carrier gas, thus reconstitution of the original cluster is hardly possible. Furthermore, in the case of FAIMS, when a certain cluster ion loses one component, quite likely its ion mobility characteristics would change, and it would be filtered out rapidly according to FAIMS principles and be lost for measurements or reconstitution. In conclusion, in the method disclosed herein the stereoselective interaction of analyte and reference compound lies in the formation of stable clusters with different spatial configuration, and declustering of analyte and reference molecule is both rare and unimportant.

Normally, no particular attention has to be paid that the stability requirement mentioned above is fulfilled. Typically, during the development of a separation method according to this document, clusters that do not meet the stability requirement and disintegrate too quickly, will not be detected or collected, or will be disregarded, as it is the intact clusters that are used for further analysis or collection. It is the actual experimental requirements, such as desired sensitivity of an analytical method, that define the required stability. If the fraction of cluster ions of interest, that survive the IMS separation, is high enough to meet any given experimental requirement, the stability requirement is met.

One related aspect is the efficiency that clusters of interest are formed with. Typically, a number of other ions are formed along with clusters of interest in the ion source. A significant fraction of the formed ions should be clusters of interest. Again, "significant fraction" means here enough clusters to allow for meaningful analysis, recovery or other experiment, as specified or required in a given experimental context.

In the actual experiments, in many cases the stability requirement and the requirement that clusters of interest are efficiently formed do not pose a major hindrance. In the examples described below, and in other experiments that are not shown in this document, no problems related to these two aspects occurred. Should problems arise in other situations, there is a large variety of possible reference compounds and experimental conditions available to solve the problem. Suitable reference compounds and experimental conditions can be determined by screening.

It should be noted that it is characteristic of the instant invention that the at least one reference substance is added to the sample before ionisation, and thus the reference molecules are present in the same physical state as the analyte itself in the sample. Clusters between analytes and at least one reference substance or reference substances are thus formed in the sample itself, or during the ionisation process, prior to IMS separation.

It is further characteristic of the instant invention that while no sample is supplied to the IMS apparatus, no reference compound has to be supplied either. This is of importance for pulsed techniques like IDM spectrometry: clusters of analytes and reference substances enter the IDM spectrometer during the sample pulse only. While no sample is supplied to the IDM spectrometer, consequently no reference compounds are supplied either. This is in contrast to Karas (WO 02096805) where reference compounds have to be added continuously to the IMS apparatus in order to achieve separation, thus using a larger amount of reference substance.

The method presented herein does not involve a derivatisation of the analyte, that generally aims for permanent covalent bonds, often involves several steps of chemistry, and often includes features such as liquid phase transitions, heat, use of different solvents, substantial waiting (reaction) times, sample clean-up after derivatisation in order to remove excess of derivatising agent or interfering side-products, and rugged chemical conditions. Rather, in the method described herein, reference substances are used in order to present a temporary asymmetric chemical environment to the chiral analyte. This is achieved through simple addition of a reference compound to the analyte, and happens very quickly, typically faster than any sample could be transported to the ionisation source. Thus the time needed for creating this asymmetric chemical environment is typically negligible for practical purposes. Normal sample pretreatment or preparation procedures, such as e.g. desalting, filtering, drying (in the case of MALDI or related techniques) can be performed before or after the addition of reference compounds to the sample, as required by the specific experiment.

It should be noted that, however critical for achieving good scientific understanding, the exact nature of the interaction between analyte and reference molecules is of lesser importance from an analytical point of view. The selection of a suitable reference compound can be done by screening, which can be successful without detailed knowledge of the inter- and intramolecular interactions during cluster formation and cluster lifetime. Typically, interactions will be of non-covalent (such as for example ionic bond, hydrogen bond, dipole-dipole interaction, Van-der-Waals forces) or weak covalent nature. In some cases, depending on the nature of interaction between analyte and reference molecules, cluster ions formed from enantiomers and reference molecules may have the nature of constitutional isomers rather than diastereomers. This fact shall in no way limit the scope of the present invention.

Not all diastereomeric clusters that are generated through the approach described herein will be readily separable by ion mobility spectrometry. Also, some clusters may be separable by IDM spectrometry but not by FAIMS, and vice versa. However, there is a great variety of chiral substances available that could potentially be used as reference compounds, and there are numerous approaches to forming diastereomeric clusters from enantiomers. One way is to form trimeric clusters with one metal ion interacting with one enantiomer molecule and two chiral reference molecules, as in the experimental examples given below.

Generally, all chiral compounds can potentially act as reference compounds. Different ways of generating diastereomeric ions from enantiomers can be envisualised. For example, a cluster ion could, apart from a metal ion, two reference molecules and an analyte molecule, also contain other components. Alternatively the two reference molecules could be replaced by one suitable larger one. Moreover, cluster ions containing two or more analyte molecules along with the reference molecule or molecules can also be used in principle. Involvement of a metal ion is often an advantage but should not be seen as a limitation of the present invention, as suitable systems not involving metal ions exist and are envisioned. Guest-host systems of a large chiral molecule (host) and a small analyte (guest), where the host is chosen in order to create stereochemically-dependent interactions with the enantiomers, is one approach. Some examples would be an enantiopure chiral crown ether, or a chiral cyclodextrin, as host and one of a pair of enantiomeric amino acids as guest. Among the chiral shift reagents used in nuclear magnetic resonance (NMR) spectroscopy, and among chiral additives in chiral capillary electrophoresis, it should be possible to find suitable compounds that form diastereomeric ions with the enantiomer analytes in the gas phase. Also, molecularly imprinted oligomers or other tailored host compounds would be useful. The principle is always the same; forming diastereomeric ions from the enantiomers by letting the enantiomers interact with compounds that allow for stereochemically-dependent interactions. One way of determining a good reference compound or good reference compounds in order to separate a given pair of enantiomers is screening. Molecular modelling may be of help as well, especially in but not limited to the case of IDM, where the relationship between molecular structure and ion behaviour in the apparatus is better understood.

It should be noted that the use of the method described herein is not restricted to situations where one enantiomer should be quantified at a large excess of the other enantiomer. Approximately equal amounts of enantiomers can be analysed as well. However, some of the methods described in the "background of the invention" section can be employed for such measurements, while most of them fail in the case of large excess of one enantiomer. That is why the focus here is on just the case of a large excess of one enantiomer.

It should be noted that once a separation method is established, the actual measurement of a sample could be performed very quickly. In case of FAIMS, only two CVs have to be monitored, when two complexes of interest, each containing one of a pair of enantiomers, are to be measured, and in most FAIMS systems two CVs can be cycled between within one second. In the case of IDM spectrometry, the separation takes typically not longer than a few hundred milliseconds. If synchronised suitably to a mass spectrometer or other means of detection, a very fast system for quantifying enantiomers would be established. In many cases the rate at which different samples can be delivered to the FAIMS or IDM spectrometry system would be the time-limiting factor.

In a similar way, chemical products, such as drugs, can be tested for contaminations by their undesired enantiomer, as a quality control. For example, drug substance would be dissolved at a certain concentration, a suitable predetermined reference substance solution would be added, and a FAIMS/MS experiment would be performed, compared to a standard curve, and the degree of contamination with the undesired enantiomer would be calculated from the result. In case the contamination with the undesired enantiomer exceeds a certain predetermined threshold value, the batch would be discarded.

Chemical processes, such as the synthesis of one enantiomer, could be monitored for the formation of the undesired enantiomer already during the process. Samples or a constant flow of reaction liquid can be taken from the reaction vessel, a suitable reference substance solution would be added or tee-ed in, and a FAIMS/MS measurement would be performed. FAIMS/MS measurements can be performed in less than one second with suitable equipment, so if samples could be delivered quickly from the reaction vessel, a close to real-time monitoring for the formation of two enantiomers would be available.

For the quantification of enantiomers that are separated according to the method described herein, analytical chemistry provides a variety of approaches including, but not limited to, the use of internal and external standards.

While probably most useful for the separation of enantiomers, other isomers, both stereoisomers and constitutional isomers, can be separated with the method described in this document. Some constitutional isomers have been shown to be separable in FAIMS and IDM spectrometry directly, without the aid of chiral reference substances. A person skilled in the art will see, however, that the method described in this document adds substantial flexibility to the separation method development for constitutional isomers. The same is true for diastereomers. In the cases of constitutional isomers and diastereomers, the method described herein can be used with the aim of separating all occurring isomers from each other, or separating one or a few isomers of interest from the other isomers. In the case of diastereomers, the formed cluster ions will normally be diastereomers as well. In the case of constitutional isomers, the formed clusters are not diastereomers, but should rather normally be regarded as constitutional isomers.

Even in cases that involve the separation of non-isomeric molecular species the approach described herein could be useful; e.g., a certain analyte ion could have unfavourable ion mobility characteristics, such as a weak dependence of the mobility on the electric field, and thus a weak FAIMS focusing effect and low ion transmission, while the same analyte as part of a larger cluster ion may experience a much stronger focusing effect due to more favourable mobility characteristics, and thus a better ion transmission in FAIMS, resulting in a more sensitive analysis. Another reason to use this approach is to move an ion from a region in the mass spectrum characterized by elevated levels of background chemical noise into a region characterized by lower levels of background chemical noise, even this potentially resulting in a more sensitive analysis.

It should be noted that the method for separating isomers, as described in this document, generally works with all kinds of ion mobility spectrometers. It is not restricted to apparatuses described within this document. Examples include: "classical" cylindrical axial IDM; IDM with slight radial electric field distortion; Triwave™ technology; differential mobility analyser (DMA); parallel-plate FAIMS; cylindrical FAIMS with off-axis ion outlet of ions (often referred to as side-to-side FAIMS); and cylindrical FAIMS with on-axis ion outlet (often referred to as domed FAIMS). Further examples include, though the technique is not limited to: hybrid instruments combining IDM or DMA with FAIMS, or combining a plurality of FAIMS units with different geometries. In no way are these examples intended to limit the scope of the patent.

In principle, the method disclosed herein works with solid, liquid or gaseous samples, provided the ionisation method is chosen accordingly. However, there is a distinct advantage with solid or liquid samples, as compared to gaseous samples. There is a much wider range of reference substances in the cases of solid or liquid samples, while in the case of gaseous samples, the choice of reference compounds is restricted to volatile reference compounds.

Various ionisation processes could be employed within the scope of this method, for example: electrospray ionisation (ESI), atmospheric pressure chemical ionisation (APCI), matrix-assisted laser desorption-ionisation (MALDI), laser desorption-ionisation (LDI), laser desorption-ionisation on silicon (DIOS), beta-emitter ionisation, photoionisation, or any other type of suitable ionisation process.

Also, various kinds of detectors could be employed within the scope of the method, for example: mass-selective detection with a mass spectrometer, or use of a Faraday plate with electrometer. A wide range of mass analysers can be employed in conjunction with the employed method, including but not limited to: linear quadrupole, triple linear quadrupole, quadrupole ion trap, linear quadrupole ion trap, time-of-flight, Fourier-transform ion cyclotron resonance, Orbitrap, magnetic/electric sector, and any hybrid instrument combining two or more modes of mass analysis. It should be noted that when employing a mass spectrometer as a detector, tandem MS (fragmentation MS) capability is not generally required. Together with or instead of a detector, means for soft landing could be employed and material collected in this way for further use or analysis.

It is possible to couple other separation techniques upstream to the ion source, such as chromatographic or electrophoretic techniques. A pre-separation of a complex sample by such a technique may lead to improved overall performance of the analytical system. Typically but not necessarily, reference substances would be added to the sample after the pre-separation; in all cases, reference substances will be added before ionisation.

FIGS. 1 to 4 illustrate in detail one example of separating and quantifying enantiomers according to the principles described in this document. Shown is the separation of clusters containing enantiomers of the amino acid tryptophan in a FAIMS apparatus. The use of this method is not restricted to the separation of amino acids. Other enantiomers of interest, namely drugs, can be separated and analysed in a similar way.

Referring to FIG. 1, shown is a mass spectrum obtained from a methanol/water (50%:50%) solution with 0.066 mM L-tryptophan (L-trp), 0.133 mM L-asparagine (L-asn) and 0.0325 mM nickel dichloride ($NiCl_2$). The solution was infused at 3 µL/min into an Agilent MSD LC ion trap mass spectrometer via its standard electrospray ionisation source. The sample was ionised at 4000 V in positive mode. As can be seen from FIG. 1, a number of ions appear in the mass spectrum. The peaks can be assigned through their mass-to-charge ratios to cluster ions formed by asparagine, tryptophan and nickel.

The cluster ion with a mass-to-charge ratio of 525 is of special interest. It is formed by one nickel ion, two molecules of asparagine and one molecule of tryptophan. In a solution that contains both tryptophan enantiomers as well as L-asparagine and nickel, the two cluster ions with the formulae $[Ni^{2+}(L\text{-asn})_2(D\text{-trp})\text{-H}]^+$ and $[Ni^{2+}(L\text{-asn})_2(L\text{-trp})\text{-H}]^+$ are diastereomers. These are indistinguishable in simple mass spectrometry; however they are potentially separable in ion mobility based systems like IDM and FAIMS.

Figure 2A:
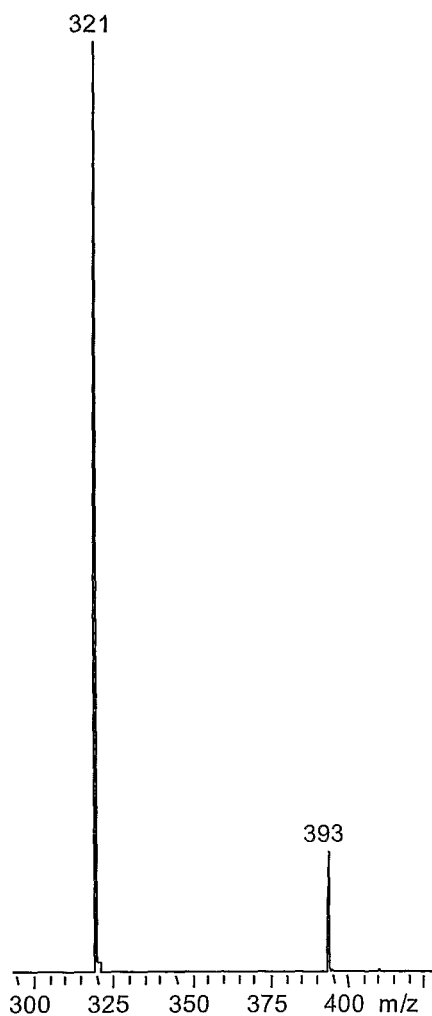
FIG. 2A is a mass spectrum diagram from tandem MS obtained from a mixture of L-tryptophan, L-asparagine, and nickel.
Figure 2B:
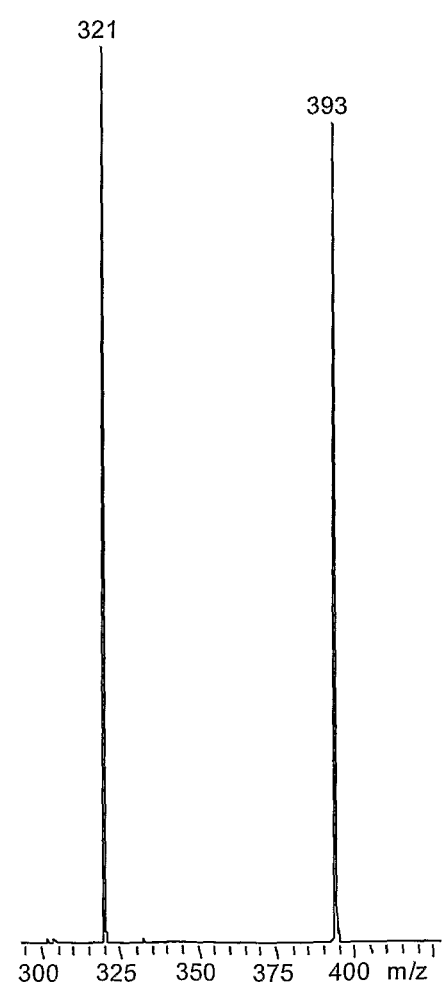
FIG. 2B is a mass spectrum diagram from tandem MS obtained from a mixture of D-tryptophan, L-asparagine, and nickel.

Referring now to FIGS. 2A and 2B, shown are tandem MS (fragmentation) spectra of ions with m/z 525, electrosprayed from a methanol/water (50%:50%) solution with 0.133 mM L-asn, 0.0325 mM $NiCl_2$ and 0.066 mM L-trp (FIG. 2A) or D-trp (FIG. 2B). The peak at m/z 321 represents loss of L-asn from the parent ion with m/z 525, while the peak at m/z 393 represents loss of L-trp and D-trp for FIGS. 2A and 2B respectively. These results show that this diastereomeric cluster ion will more easily lose D-trp than L-trp, implying that this fragmentation pattern provides an indirect means of distinguishing between the presence of the L- and D-forms of tryptophan therein; however, they are not actually physically separated. FIGS. 1 and 2 represent prior art. MS and tandem MS settings for experiments associated with FIGS. 1 and 2 were identical with settings specified below for FIG. 3, except for the ionisation part. Herein, this prior art is exploited to aid in confirmation of separation of diastereomers by the new methodology proposed in the present patent application.

The FAIMS apparatus used for this work was a domed-type cylindrical FAIMS apparatus; i.e. a type of FAIMS interface where the ion inlet is on the side of the outer cylinder, and the ion outlet on the axis of the cylinders. The analytical gap had a width of 2.0 mm and was in between two concentrically aligned cylinders, with the inner cylinders' outer diameter being 10 mm and the outer cylinders inner diameter being 14 mm. The distance between inner and outer cylinder was 2.5 mm at the tip of the inner cylinder. Carrier gas (3L/min, 60% nitrogen, 40% helium, room temperature, ambient pressure) was supplied to a space between the ion inlet and the front plate. The front plate was kept at +900V, the outer cylinder at ground potential, and the inner cylinder received a dispersion voltage (DV) of nominally −4000V, following the equation $U=(2\ \sin(2*\pi*f*t)+\sin(4*\pi*f*t-\phi))*1333V$, U being the voltage, the frequency f being approximately 750 kHz, and the phase shift $\phi$ being $\pi/2$. Also, a variable direct current (dc) compensation voltage (CV) was supplied to the inner cylinder. The ion outlet was in communication with an Agilent 1100 series MSD ion trap mass spectrometer (MS). The FAIMS apparatus was attached to the MS via a simple PEEK support, in such a way that the FAIMS ion outlet was located at approximately 1 mm distance from the MS inlet capillary. The tip of the MS inlet capillary was kept at ground potential. Into the gap between FAIMS ion outlet and the MS ion inlet, a make-up gas of 0.15 L/min nitrogen was supplied. An electrospray needle (stainless steel microspray needles with an internal diameter of 50 µm) was positioned in communication with the FAIMS front plate, and kept at +3400V. The mass spectrometer was used at the following settings: MS capillary exit (128.5 V); skimmer (40 V); lens 1 (−5 V); octopole 1 dc offset (12 V); octopole 2 dc offset (1.7 V); octopole rf amplitude (178.1 Vpp); partition (6.8 V); lens 2 (−60 V); and trap drive (46.7 V). The following tandem MS settings were used, when tandem MS was employed: isolation width (4 m/z); and fragmentation amplitude (0.8 V). The tandem MS isolation m/z was set in each experiment to suit ions of the general formula $[M(Ref)_2(A)\text{-H}]+$, where M is the metal ion, Ref is the chiral reference compound, and A is the chiral analyte of interest. These electrospray, FAIMS, MS and tandem MS parameters were used throughout all experiments presented below, unless explicitly stated otherwise.

Figure 3A:
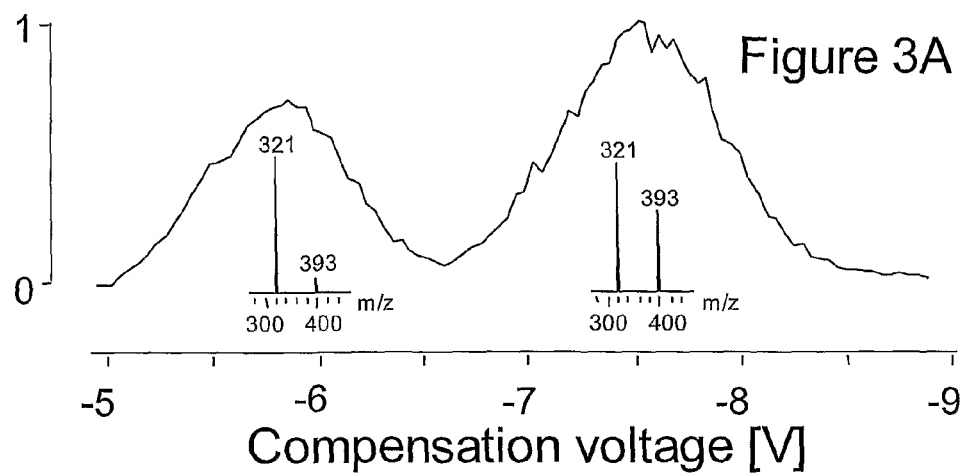
FIG. 3A is an extracted ion chromatogram from a tandem MS measurement of a CV scan of ions generated from a mixture of L-tryptophan, D-tryptophan, L-asparagine, and nickel.
Figure 3B:
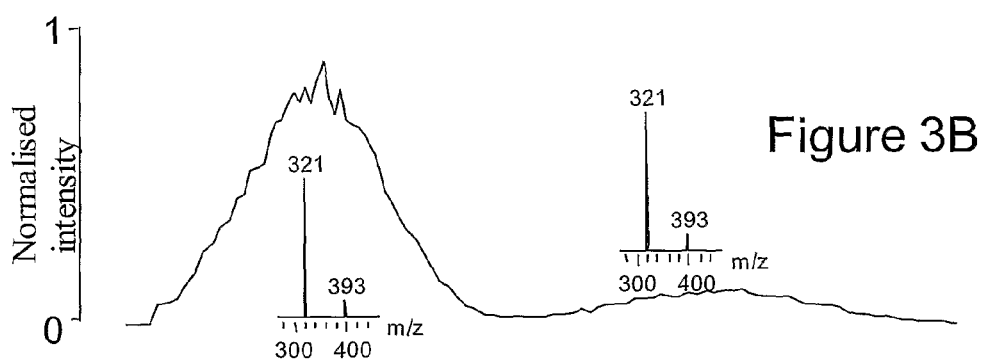
FIG. 3B is an extracted ion chromatogram of a CV scan from a tandem MS measurement of ions generated from a mixture of L-tryptophan, L-asparagine, and nickel.
Figure 3C:
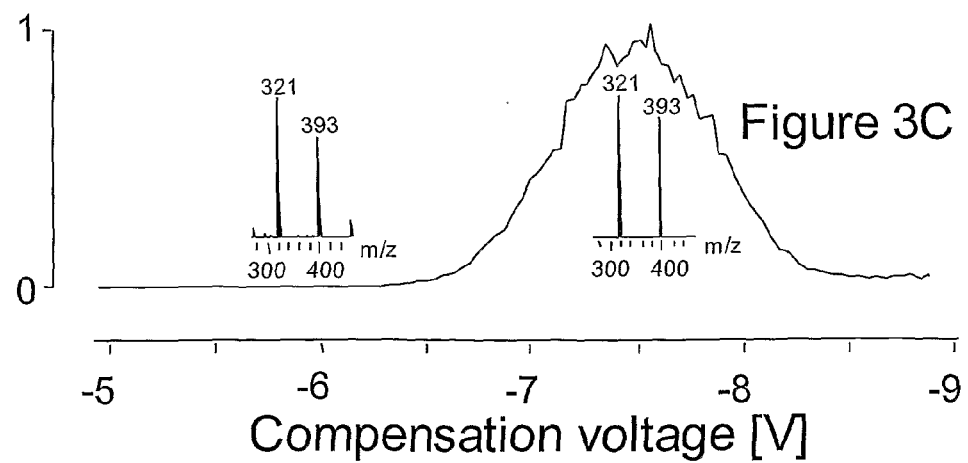
FIG. 3C is an extracted ion chromatogram of a CV scan from a tandem MS measurement of ions generated from a mixture of D-tryptophan, L-asparagine, and nickel.

Referring now to FIGS. 3A-C, shown are results of CV scans of different samples. During these experiments, the mass spectrometer was operated in tandem (fragmentation) mode with parent ion at m/z 525 (though MS/MS is not a required feature of the present invention). The traces represent the intensities of ions with the mass-to-charge ratio (m/z) 321 and 393 added. The m/z 321 and 393 correspond to the loss of trp or asn from the parent cluster ion. The CV is scanned from −5V to −9V within 8 minutes. Samples are infused at a flowrate of 1 µL/min. Mass spectra at the peak maxima in the traces are inset close to the respective peaks. It should be noted that the same tandem MS parameters were used for the results shown in FIGS. 2A-B and 3A-C. Namely, the collision induced dissociation (CID) voltage was set to 0.8V.

FIG. 3A shows results from a sample solution containing 0.066 mM D-trp, 0.066 mM L-trp, 0.133 mM L-asn and 0.0325 mM nickel dichloride, with methanol/water (50%: 50%) as solvent. Two distinct peaks can be observed in the extracted ion chromatogram, centred around CVs of −5.9V and −7.6V. The appearance of these two peaks suggests the separation of the two diastereomers by FAIMS alone. To confirm conclusions, the kinetic fragmentation method of Tao was further employed. The results, shown in FIG. 3A, can be directly compared to the results shown in FIG. 2. The relative intensity of the fragments with m/z 321 and 393 at CV=−5.9 suggests that this peak in the CV scan is caused by the cluster ion $[Ni(L\text{-asn})_2(L\text{-trp})\text{-H}]^+$, according to FIG. 2A. The relative intensity of the fragments at CV=−7.6 suggests that this peak in the CV scan is caused by the cluster ion $[Ni(L\text{-asn})_2(D\text{-trp})\text{-H}]^+$.

Referring now to FIG. 3B, shown are results from a sample solution containing 0.066 mM L-trp, 0.133 mM L-asn and 0.0325 mM nickel dichloride, with methanol/water (50%: 50%) as solvent. One distinct peak is observed at CV=−5.9V. The relative intensity of the fragments with m/z=321 and 393 at CV=−5.9 suggests that this peak is caused by the cluster ion $[Ni(L\text{-asn})_2(L\text{-trp})\text{-H}]^+$, consistent with the conclusion about the results presented in FIG. 3A. However, a smaller peak can be observed at a CV of −7.8V. This peak could not be attributed to an impurity of D-trp—the substances employed had a purity of greater than 99%, and moreover, the relative intensity of the fragments at CV=−7.8V suggests that this peak is not caused by the cluster ion $[Ni(L-asn)_2(D-trp)-H]^+$. (Note that this peak in the CV spectrum is actually shifted slightly with respect to the peak at CV=−7.6 V in FIG. 3A.) One possibility is that the peak represents a second cluster ion with the same formula $[Ni(L-asn)_2(L-trp)-H]^+$ but with a different conformation as compared to the ions giving rise to the peak at CV=−5.9V.

Referring now to FIG. 3C, shown are results from a sample solution containing 0.066 mM D-trp, 0.133 mM L-asn and 0.0325 mM nickel dichloride, with methanol/water (50%: 50%) as solvent. Now only the peak centred at CV=−7.6 V is present, with no peak visible at CV=−5.9V, well in line with the notion that only D-trp is present. As a confirmation, the relative intensities of the fragments observed at CV=−7.6 V compared with FIG. 2B is consistent with this peak being caused by the cluster ion $[Ni(L-asn)_2(D-trp)-H]^+$. At CV=−5.9V, no peak is observed, however there is some tailing from the peak at −7.6V. A mass spectrum for CV=5.9V is inset in FIG. 3C; the total intensities of all fragments in this mass spectrum are very low.

FIGS. 3A-C thus demonstrate a successful separation of a pair of enantiomers with FAIMS. This is made possible by creating an asymmetric chemical environment and letting the pair of enantiomers interact with that environment, in such a way that a pair of diastereomers is formed. It is these diastereomers that then, after ionisation, can be separated by FAIMS. The formation of other cluster ions along with the ions of m/z=525, in this example, as shown in FIG. 1, is not a problem as long as a significant fraction of the formed cluster ions have a m/z of 525. In this example, each of the generated pair of diastereomeric cluster ions consists of one metal ion, two chiral reference molecules, and one molecule of one of a pair of enantiomers that are desired to be separated from each other, this cluster ion being deprotonated.

Referring now to FIG. 4, shown is an example of a quantitative measurement using the method described in this document. The scope of the example is to create a calibration curve for quantifying the presence of an undesired enantiomer (L-trp in this example) in the presence of a large excess of a desired enantiomer (D-trp in this example). The calibration curve could then be used to determine the enantiomeric excess of a product (D-trp in the example).

Figure 4A:
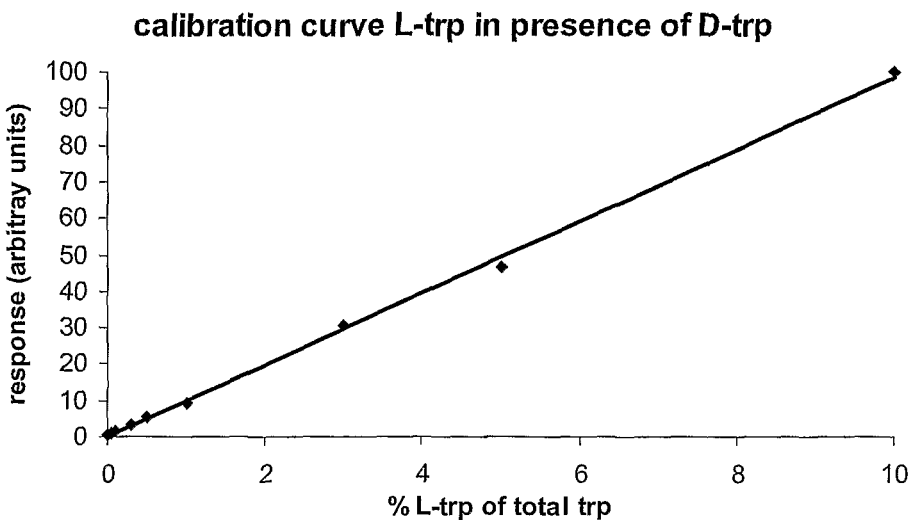
FIGS. 4A and 4B are calibration curves for L-tryptophan in presence of an excess of D-tryptophan, for different concentration ranges.
Figure 4B:
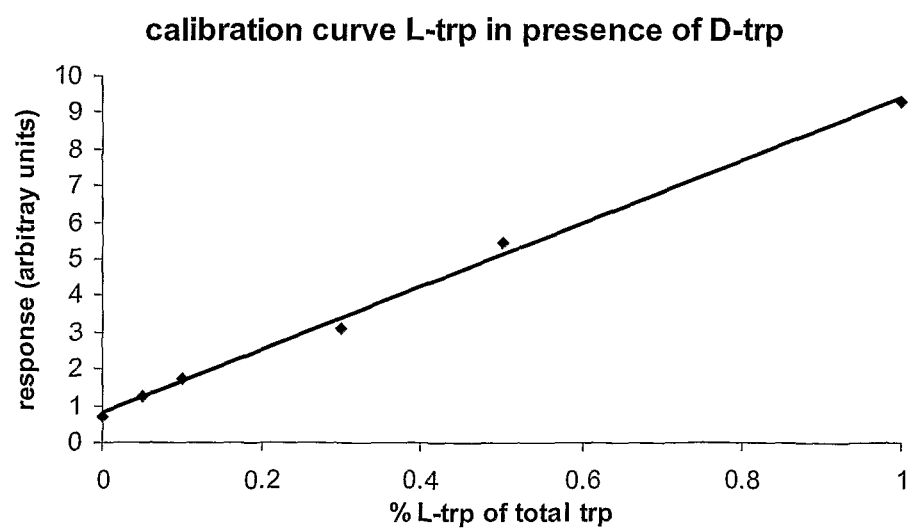

In FIG. 4A-B, shown are calibration curves of L-trp in the presence of D-trp at a total trp concentration of 0.1 mM, the solutions also containing 0.2 mM L-asn, and 0.05 mM $NiCl_2$ in methanol/water (50%:50%). At higher concentrations of L-trp, concentrations of D-trp decrease, the L-trp and D-trp concentrations always adding up to 0.1 mM. This is intended to simulate unknown samples, where only a total concentration will be known from weighing the sample. The same system described above is employed for analysis, except that signals are only monitored at FAIMS CV settings of −5.9V and −7.6V, which are the maxima for L-trp and D-trp transmission, respectively, in this experiment. The signal intensity for the cluster of the undesired enantiomer, $[Ni(L-asn)_2(L-trp)-H]^+$, is corrected using the signal intensity of $[Ni(L-asn)_2(D-trp)-H]^+$ as internal standard. The two calibration curves are generated from the same data, but show different concentration ranges: 0% to 10% L-trp (FIG. 4A) and 0%-1% L-trp (FIG. 4B). It can be seen that the calibration curves in this example show a good linearity in the concentration range between 0.1% and 10% L-trp. Some background signal from the tail of the $[Ni(L-asn)_2(D-trp)-H]^+$ peak, as shown in FIG. 3C, is present at a CV of −5.9 as well, limiting in this case the sensitivity to about 0.1% undesired enantiomer (L-trp), corresponding to an enantiomeric excess of 99.8%.

In the complementary case that it was the D-trp that should be quantified in a large excess of L-trp, the peak at CV=−7.8V in FIG. 3, originating from L-trp, would substantially limit the usefulness of this method, because it would represent a large background signal. A solution would be the use of D-asn as reference compound instead of L-asn. The signal of the cluster $[Ni(D-asn)_2(D-trp)-H]^+$ would then have the same position as the cluster $[Ni(L-asn)_2(L-trp)-H]^+$ has in FIG. 3B, while the signal from $[Ni(D-asn)_2(L-trp)-H]^+$ would look the same as the signal from $[Ni(L-asn)_2(D-trp)-H]^+$ in FIG. 3C, and quantification of D-trp would be straight-forward using the same approach as described above. This change of peak positions has been demonstrated experimentally, however the results are not presented herein.

If available, the use of isotopically marked analogues of the analyte of interest as internal standard is possible. This would also eliminate the small mistake that is introduced in the calibration curves of FIG. 4A-B, where the signal from $[Ni(L-asn)_2(D-trp)-H]^+$ is used as internal standard, neglecting the fact that the concentration of D-trp in fact is not constant in this case, as it varies between 0.09 and 0.1 mM.

Figure 5A:
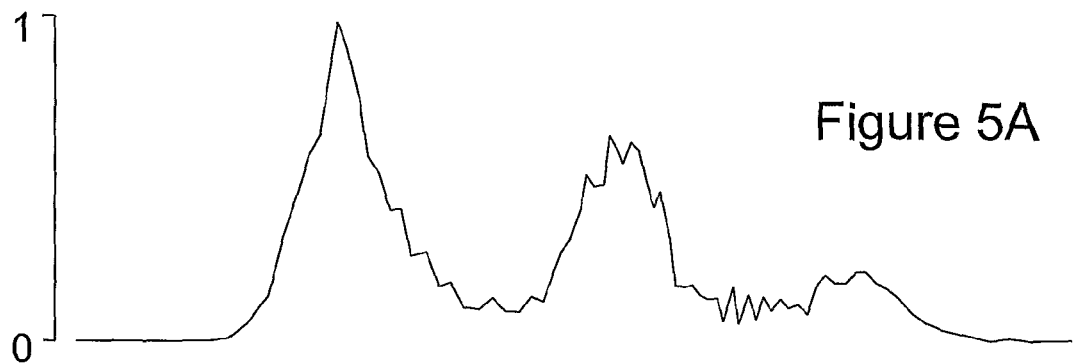
FIGS. 5A, 5B and 5C are extracted ion chromatograms and illustrate the separation of D/L-valine in the presence of magnesium and L-isoleucine, similar to FIGS. 3A, 3B and 3C.
Figure 5B:
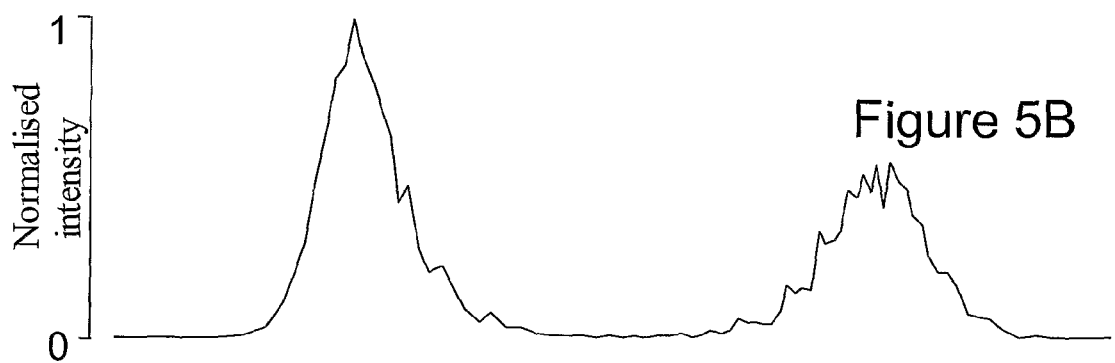
Figure 5C:
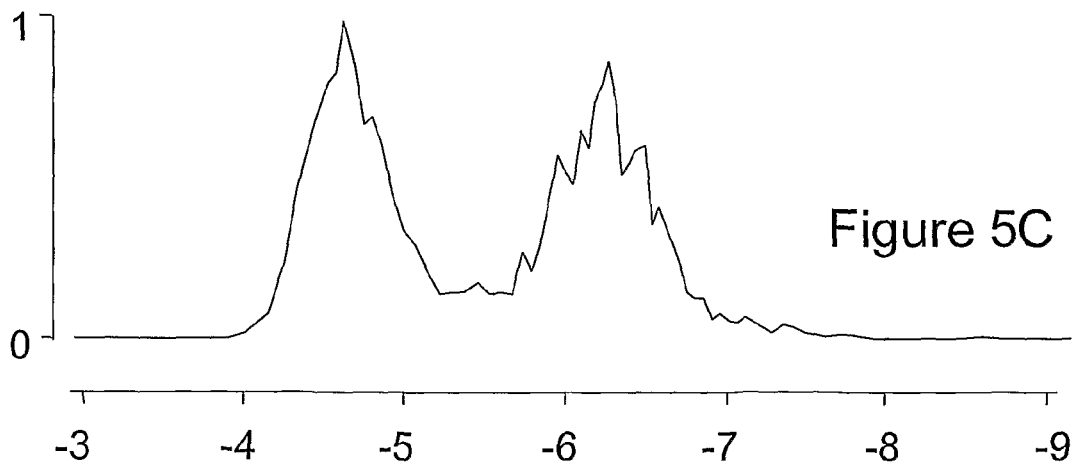

Referring now to FIG. 5A-C, shown is another separation of enantiomers, using the same method as described above, except that the pair of enantiomers is D/L-valine (D/L-val), the chiral reference substance is L-isoleucine (L-ile), and the metal ion is magnesium ($Mg^{2+}$). The concentrations of all chemicals are analogous to the concentrations in the experiments associated with FIG. 3. The distance between inner and outer FAIMS cylinders was 2.7 mm at the tip of the inner cylinder. The trace shown in FIGS. 5A-C is an extracted ion chromatogram at m/z=402, from a simple mass measurement (no tandem mass spectrometry). Apart from L-ile and $Mg^{2+}$, samples contain D-val and L-val (FIG. 5A), only L-val (FIG. 5B), and only D-val (FIG. 5C). Interestingly, one peak at CV=−4.5V is present in all samples, while the peak at CV=−6.2V is associated with the presence of D-val, and the peak at CV=−7.8V is associated with the presence of L-val. The peaks at CV=−6.2V and CV=−7.8V could be used for quantification of D-val and L-val in the presence of each other. It cannot be concluded from the data presented herein, why a plurality of peaks is present in each case here for each pure enantiomer analyte. One explanation is that clusters with the same formula can assume different conformations whose formation is approximately equally favoured. It is conceivable, that even more such peaks could be observed in other examples, or that only one enantiomer has the capability of forming several different conformations with a certain reference compound. This does not generally limit the method described herein, as long as at least one peak appears that is specifically associated with the occurrence of one certain enantiomer.

Referring now to FIG. 6, shown is a summary of successful separations of 7 pairs of amino acid enantiomers. In these cases, the CV was scanned from 0 to −16V in 8 minutes, and the mass spectrometer was operated in tandem MS mode. For all analytes of interest, several different successful combinations of metal ions and chiral reference compounds have been found by screening. In all experiments, the L form of the reference compound has been used, although the D form would work equally well. In FIG. 6, short forms denote: trp (tryptophan), pro (proline), phe (phenylalanine), val (valine), met (methionine), arg (arginine), lys (lysine), gin (glutamine), asn (asparagine), ile (isoleucin), Mg (magnesium), Cu (copper), Ni (nickel), Zn (zinc).

Apart from ion mobility spectrometric techniques, other techniques are conceivable that separate ions in the gas phase according to molecular properties other than mass-to-charge ratio. The method described in this document could in some cases be adapted to such other techniques, still following the general principles of complex ion formation and separation as described herein.

It should be noted that although the method in this document has been described for gas phase separations, it is conceivable that the method would work in other phases, such as liquid or supercritical phase, as well. In such cases, experimental conditions and setup have to be adapted to the respective technique, namely the means of ionisation and ion detection. Still the same general principles of complex ion formation with subsequent separation as described in this document would be followed.

Further modifications may occur to a skilled person reading this specification and such modifications are intended to be included within the scope of the present invention.

In the claims and the specification, the term "comprises/comprising" does not exclude the presence of other elements or steps. Furthermore, although individually listed, a plurality of means, elements or method steps may be implemented. Additionally, although individual features may be included in different claims, the individual features may be combined separately in other combinations, and the inclusion of the features in different claims does not imply that another combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

Although the present invention has been described above with reference to specific embodiment, it is not intended to be limited to the specific form set forth herein. Rather, the invention is limited only by the accompanying claims and other embodiments than those described above are equally possible within the scope of the appended claims.

The invention claimed is:

1. A method for separating and detecting molecules comprising the steps of: a) providing a sample comprising at least one first chiral molecular species, and providing at least one second chiral molecular species, b) adding said at least one second chiral molecular species to said sample before ionisation, c) providing at least one ionisation source for generating diastereomeric cluster ions from said sample, d) separating said generated diastereomeric cluster ions on the basis of their molecular characteristics, and e) detecting the ratio of said diastereomeric cluster ions to determine the enantiomer percentage of said first chiral molecular species in the sample.

2. The method as claimed in claim 1, wherein said diastereomeric cluster ions are composed of said at least one first chiral molecule and said at least one second chiral molecule.

3. The method as claimed in claim 1, wherein said diastereomeric cluster ions are present in the gas phase.

4. The method as claimed in claim 1, wherein said separation is provided by an ion mobility spectrometry apparatus.

5. The method as claimed in claim 1, wherein the physical state of said sample is one of solid or liquid.

6. The method as claimed in claim 1, wherein said at least one first chiral molecular species is at least one of a pair of enantiomers.

7. The method as claimed in a claim 4, wherein said ion mobility spectrometry apparatus is a FAIMS apparatus.

8. The method as claimed in claim 1, wherein at least one non-chiral compound, such as metal ions in solution, is added to said sample before ionisation.

9. The method as claimed in any of claim 1, wherein said at least one second chiral compound and optionally said at least one non-chiral compound are chosen in such a way that a significant fraction of said diastereomeric cluster ions have sufficiently high stability in order to survive during said diastereomeric cluster ions' residence in said ion mobility spectrometry apparatus.

10. The method as claimed in any of claim 4, which includes providing an analytical instrument, such as a mass spectrometer or an electrometer, for quantifying diastereomeric cluster ions, or providing a means for collecting diastereomeric cluster ions, said analytical instrument or means for collecting diastereomeric cluster ions being in communication with at least one ion outlet of said ion mobility spectrometer, in order to allow for analysis or recovery of ions transmitted by said ion mobility spectrometry apparatus.

11. The method claimed in claim 10, which includes subjecting said diastereomeric cluster ions to mass spectrometric analysis in order to quantify the enantiomeric excess of a compound in a sample of interest.

12. The method claimed in claim 1, wherein said at least one ionisation source is at least one of the group of electrospray ioniser, atmospheric pressure chemical ioniser, beta-emitter, or MALDI.

13. The method claimed in claim 6, wherein said diastereomeric cluster ions contain at least one metal atom or ion, at least one of a pair of enantiomers, and at least one chiral molecule.

14. The method claimed in claim 1, wherein said diastereomeric cluster ions are composed of one metal ion, at least one of a pair of enantiomers, and two molecules of a chiral reference compound.

15. The method as claimed in claim 4, wherein at least one non-chiral compound, such as metal ions in solution, is added to said sample before ionisation.

* * * * *